United States Patent [19]
Alexander et al.

[11] Patent Number: 5,064,083
[45] Date of Patent: Nov. 12, 1991

[54] CLOSURE DEVICE

[75] Inventors: Barbara Alexander, Collegeville; Patty H. Kiang, Paoli; Richard Lusch, Phoenixville; Val Romberg, Parkerford, all of Pa.

[73] Assignee: The West Company, Incorporated, Phoenixville, Pa.

[21] Appl. No.: 493,144

[22] Filed: Mar. 8, 1990

[51] Int. Cl.⁵ .............................................. B65D 39/18
[52] U.S. Cl. ...................................... 215/247; 215/364
[58] Field of Search ................. 215/247, 354, 355, 364

[56] References Cited

U.S. PATENT DOCUMENTS

| | | | |
|---|---|---|---|
| 4,316,941 | 2/1982 | Eguchi et al. | 428/421 |
| 4,554,125 | 11/1985 | Knapp | 264/266 |
| 4,635,807 | 1/1987 | Knapp | 215/247 |
| 4,756,974 | 7/1988 | Romberg | 428/423.9 |
| 4,808,453 | 2/1989 | Romberg et al. | 428/36.8 |
| 4,915,243 | 4/1990 | Tatsumi et al. | 215/247 |
| 4,973,504 | 11/1990 | Romberg et al. | 428/36.8 |
| 5,000,994 | 3/1991 | Romberg et al. | 428/36.8 |

FOREIGN PATENT DOCUMENTS 0294127  12/1988  European Pat. Off. ............ 215/364

Primary Examiner—Stephen Marcus
Assistant Examiner—Stephen Cronin
Attorney, Agent, or Firm—Eugene E. Renz, Jr.

[57] ABSTRACT

A device for use with containers, including an elastomeric member sized to engage the container. The member has a first portion for contact with the container to form a seal and a second portion having a polyparaxylylene coating to form a barrier between the member and the contents of the container.

5 Claims, 3 Drawing Sheets

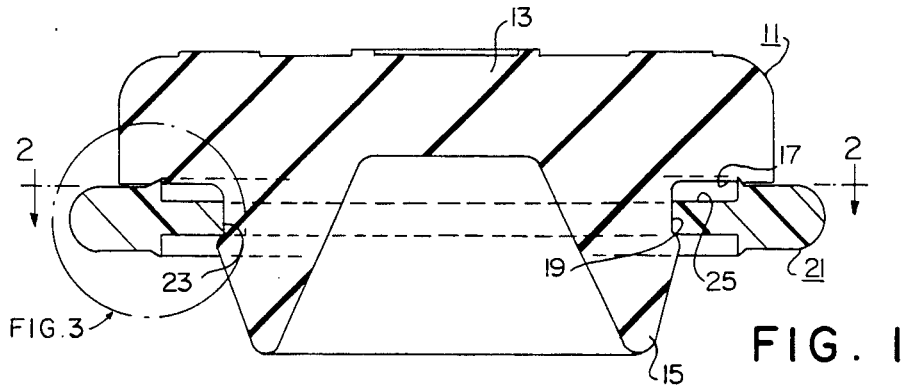
FIG. 1
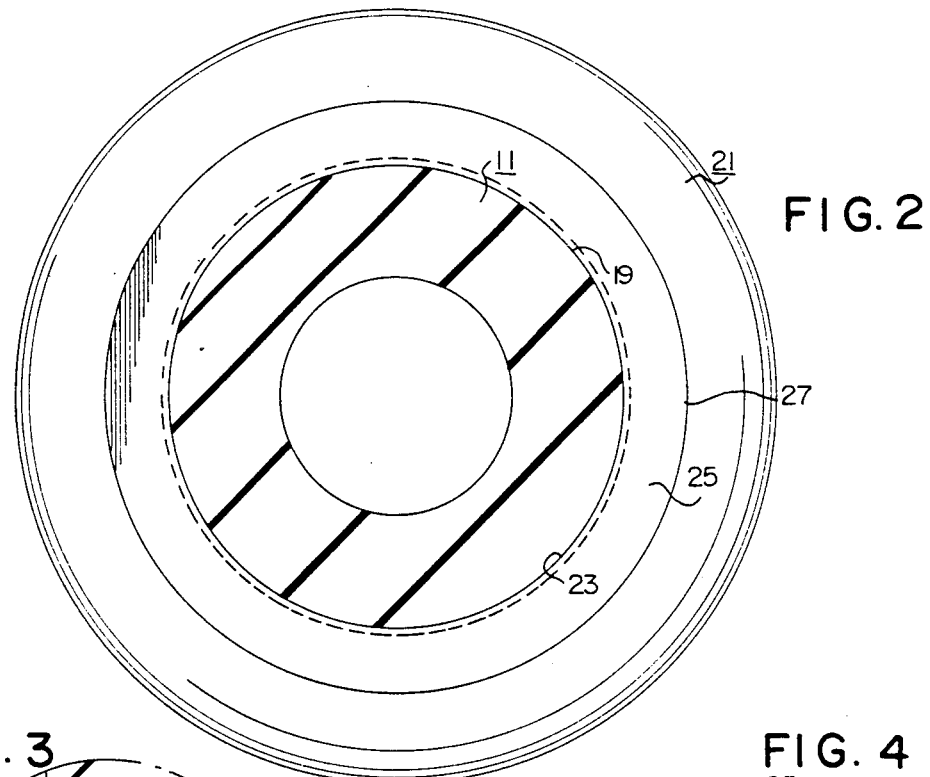
FIG. 2
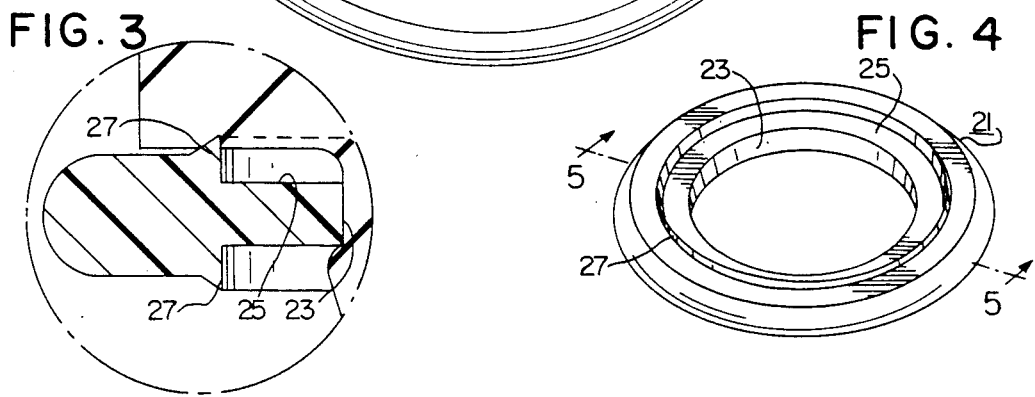
FIG. 3
FIG. 4

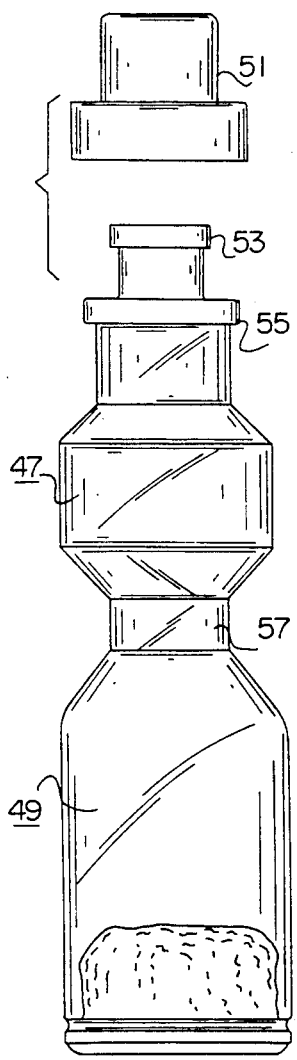
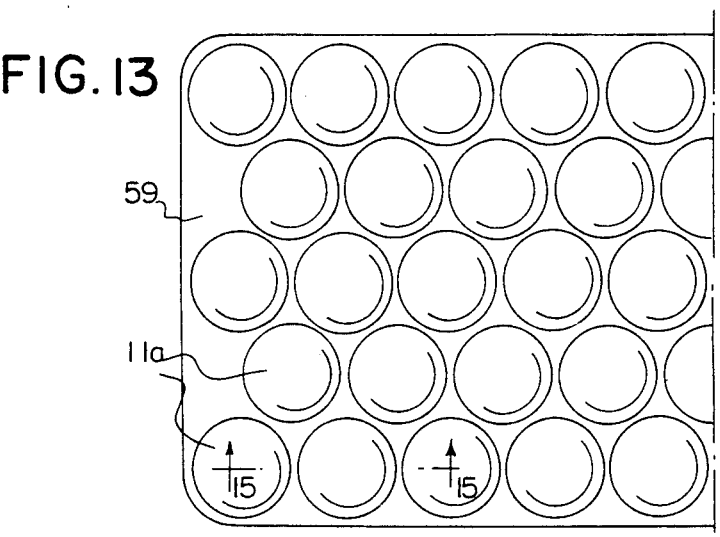
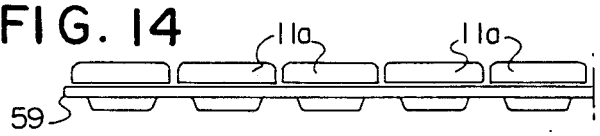
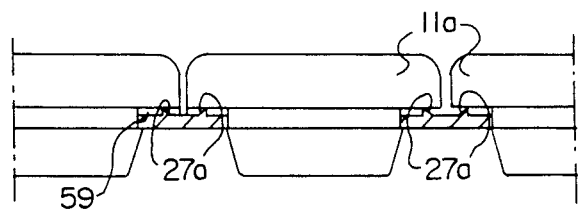
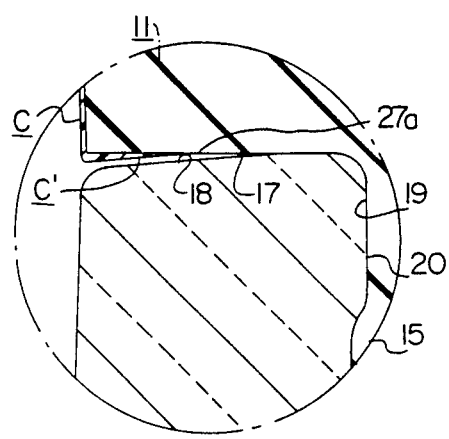

CLOSURE DEVICE

FIELD OF THE INVENTION

This invention relates to a device for use with containers, such as pharmaceutical containers, syringes and the like made from glass or plastic. The device of the present invention comprises an elastomeric member which forms an efficient seal and which includes a barrier to prevent contact of the contents of the container with the elastomeric member.

BACKGROUND OF THE INVENTION

For many years, the most successful container system for pharmaceutical products has been the combination of elastomeric members in glass vials or other containers such as syringes, bottles and the like. The glass and rubber combination has been useful for a wide variety of pharmaceutical ingredients, combining both safe storage of the medicine and easy access through the elastomeric member. A needle can easily penetrate the rubber stopper to withdraw the desired amount of liquid in a vial without otherwise interfering with the integrity of the closure. Even when powders are stored in vials, the elastomeric member can be penetrated with a needle to activate the powder by adding liquids such as pure water. The activated medicine remains in a safe, protected environment.

The glass and rubber interface has provided reliable seals and a relatively inert environment for the medicaments. For example, in syringes, the syringe tip may be manufactured from an elastomeric material. Its function is to slide along the interior wall of the syringe while maintaining a seal between the syringe tip and the cartridge. At the same time, the syringe tip made from elastomeric materials should not contaminate the contents of the syringe. Sleeve stoppers, elastomeric caps, flash back bulbs, center seals between two compartment vial packages and other elastomeric members have also been found to be useful in combination with glass and plastic objects not only in the pharmaceutical industry but in other industries.

Because of the success of these types of pharmaceutical devices, and as more and more systems have been using rubber in combination with glass containers, the rate at which these devices can be assembled contributes greatly to the economic efficiencies of this otherwise desirable component design. For example, conventional pharmaceutical assembly machines which are useful for filling vials rely on a mechanical implantation of a rubber stopper into the neck of the vial or other shaped container. Just prior to the mechanical insertion, the rubber stoppers are transported from the hopper to the stoppering equipment, usually by centrifugal, vibrating or gravity feed. It is essential that the rubber components not hang up on each other or on the transfer equipment. It is essential that they flow smoothly into the capping or closure forming device. Plastic containers are also becoming more useful in pharmaceutical containers.

The equipment used for transferring components is typically made from stainless steel or other materials which can be kept extremely clean for pharmaceutical purposes. The ability of the rubber component to move smoothly on the surface is directly dependent upon its coefficient of friction, with lower values for coefficient of friction being far more desirable. Also, it is at least as important that the elastomeric components do not stick to one another during travel through this transfer equipment.

In Romberg et al U.S. Pat. No. 4,808,453, an elastomeric stopper is described which is suitable for use with containers, wherein the co-efficient of friction of the stopper is reduced to less than about 1.0 through the use of a continuous polyparaxylylene coating. Stoppers and other elastomeric materials which are manufactured according to Romberg et al function effectively in mechanical hoppers and stoppering equipment generally. In addition, the pharmaceutical elastomeric coatings described in Romberg et al have been able to protect the contents of the container from contamination by extractable metals in the elastomeric base material. The use of silicone oil as a lubricant to prevent rubber products from sticking or binding to one another is also eliminated. Elimination of the silicone oil greatly reduces a source of particles which, while not particularly harmful or undesirable by themselves, are included in the total particle count. The Food and Drug Administration places a maximum on the number of particles present, without concern for the source of the particles. Thus, silicone oil is to be avoided.

Similarly, elastomeric materials which are used in the pharmaceutical industry have been carefully selected and formulated to be as inert as possible when in contact with pharmaceutical products such as medicines and the like. Formulations and products are checked constantly to determine that they are not being contaminated. Of particular importance, in addition to the above mentioned particle count produced by silicone oil, are particles which are extracted from the elastomeric closure itself. Certain trace metals are employed in the manufacture of elastomeric compounds, such as catalysts and other additives. It is essential that no extraction of these materials take place by the liquids which come in contact with the elastomeric member. Of particular concern are metals such as calcium and aluminum, and heavy metals such as zinc and lead. Accelerated and ultra vigorous testing is used to determine the amount of these undesirable materials which potentially may be extracted from the rubber. If the actual quantity of extractable metals present after vigorous testing is within the "safe" level, then the use of the elastomeric material under normal conditions would likely result in a nearly contamination free product.

Gorham U.S. Pat. No. 3,288,728 discloses a basis method of preparing linear co-polymers from paraxylylenes using temperature conditions between 450° C. and 700° C. This patent suggest that small articles can be protected or encapsulated with these polymers to obtain the insulative and protective properties of the polyparaxylylenes. The patent generally suggests that there are enumerable possible applications for the polymer as a coating material.

Gorham U.S. Pat. No. 3,342,754 describes the broad method of preparing linear polymers of paraxylylene and particularly in preparing coatings using this material. The patent is replete with a variety of examples of variations and suggests that these polymers are desirable for use as a film, fiber, surface coating, or electrical insulation. Both this patent and the previous Gorham patent offer the general suggestion that almost any material may be coated with paraxylylene polymers, although neither has a specific example relative to the pharmaceutical industry.

U.S. Pat. No. 3,379,803 describes apparatus and methods useful for polymerizing paraxylylene and applying this material as a continuous film on a wide variety of substrates. U.S. Pat. No. 4,225,647 discloses a process for coating an extremely broad list of materials with polymers of paraxylylene. This patent suggests that a first layer of substituted silicon compounds be employed prior to the polyparaxylylene coating.

Gorham et al U.S. Pat. No. 3,300,332 describes a coating process wherein an object is to be coated with an insoluble coating. The thickness is not described in detail, but Gorham suggests that the thickness is not narrowly critical. He describes a coating of 0.1 mil as being very thin and useful when desiring resistance to solvents or reactive attack. In one example, six rubber stoppers are coated to protect them from solvents such as heptane. The amount of coating added ranges from 0.22 to 0.28 grams, which would indicate a thickness of at least 1 mil when standard stoppers are used. Tests have been run which clearly demonstrate that stoppers of the Gorham et al U.S. Pat. No. 3,300,332 are totally non functional as stoppers. In one test, taking the thinnest possible coating, 4 out of 10 stoppers were unable to seal at all. Needle penetration increased by almost a factor of two when compared to an uncoated stopper, again rendering the Gorham et al stoppers unacceptable in the pharmaceutical industry. Of course, Gorham et al does not even suggest that a coating can be used with drugs and the like.

Rubber coatings for pharmaceutical vials are quite old in the art. U.S. Pat. No. 2,649,090 discloses a rubber closure for pharmaceutical vials. U.S. Pat. No. 2,734,649 provides a stopper which is dipped to a desired depth with a coating as an alternative to spraying of the coating on the stopper. U.S. Pat No. 2,747,765; U.S. Pat. No. 4,441,621; and U.S. Pat. No. 4,635,807 all disclose relatively thick coatings on stoppers for various purposes. It has been found in each of these patents the coating itself is incapable of forming a barrier between the stopper and the contents of the vial. In some cases the coating itself is elastomeric and therefore contains those same extractable metals and other impurities which are to avoided.

Finally, U.S. Pat. No. 3,375,110 and U.S. Pat. No. 3,395,016 both disclose the use of polyparaxylylene on the surface of an etchable substrate. Similarly, U.S. Pat. No. 3,375,419 employs etching techniques to place polyparaxylylene film in an area of a transistor device which requires an insulating film. Hofer U.S. Pat. No. 3,895,135 teaches treatment of electrical substrates and suggests that non electrical substrates may also be coated. Hofer describes a constricted flow path along an interface between a masked and unmasked surface with a particular ratio of length to height of about 60 to 1 and preferable 120 to 1. None of these last mentioned patents even address the possibility of applying a polyparaxylylene coating to stoppers and other closures for containers and other devices, particularly in the pharmaceutical industry.

Accordingly, it is an object of this invention to provide a new device for use with pharmaceuticals in which a truly effective seal can be achieved without contamination of the contents.

Another object of this invention is to provide a method for applying a suitable coating to elastomeric closures which provides for an effective seal without contamination.

SUMMARY OF THE INVENTION

Accordingly, it has now been discovered that an improved product may be prepared for use with pharmaceuticals and the like. The product comprises an elastomeric member which is sized to engage a vial or other container for pharmaceutical goods or other very sensitive ingredients or components, particularly where high purity and lack of contamination are a major concern. The elastomeric member has a first portion for contact with the container to form a seal and a second portion having a polyparaxylylene coating to form a barrier between the member and the contents of the container.

The elastomeric member of this invention may be manufactured from any conventional elastomeric base material which has been used in pharmaceutical devices where an elastomeric component is required. Such materials are formed into rubber stoppers, plunger tips, prefilled syringes, sleeve stoppers, flashback bulbs, caps, liners, washers and other elastomeric members which are in contact with the contents of a container in which there is a pharmaceutically pure material.

The elastomeric component of the present invention may be manufactured from any of the elastomeric compounds which have conventionally been used in the pharmaceutical industry and other industries where elastomers are used to make closures. Natural rubber, of course, was the original choice of materials for many elastomeric formulations and components. Butyl rubber and many of the synthetic elastomers have been successfully used as stoppers, plunger tips, and the like, depending upon requirements for stability during autoclaving or sterilization. A particular rubber which is admirably suited for the purposes of this invention is butyl rubber. The elastomeric member should be selected from an elastomer which is capable of forming a seal with glass so that the seal has a vacuum retention of at least about 96% or more and where the seal integrity is about 0.1 mg or less, as defined hereinafter. Glass to elastomer interfaces are of primary importance if suitable product integrity is to be achieved.

Polymers made from the various paraxylylenes may be applied as a coating in the manner which has previously been described in the various patents discussed herein above. Specifically, as an example of various paraxylylene polymers and co-polymers, the previously referenced Gorham U.S. Pat. Nos. 3,342,754 and 3,288,728 describe the chemistry of the polymers and co-polymers which may be employed as coatings in the present invention. The Tittman et al U.S. Pat. Nos. 3,379,803 and 3,472,795 described suitable methods for applying these particular polymers and copolymers on to a wide variety of materials. It has been found that these processes generally are suitable for applying polymers and co-polymers of paraxylylene to elastomeric base materials contemplated in the present invention. The term polyparaxylylene is intended to include both polymers and co-polymers of the various paraxylylenes which are described in the prior art. The coating should be applied to the appropriate region to achieve a thickness of at least 0.1 microns, and preferably 0.5 to 1.0 microns. The maximum thickness can be as great as 5.0 to 25 microns or more.

The barrier portion formed by the paraxylylenes prevents the contents of the container from acting on the elastomer, so that impurities in the elastomer are not extruded or leached out. It is desirable to reduce extractables to an absolute minimum. As will be explained below, the present invention is unique in being able to form a seal equal to uncoated elastomer to glass seals while also eliminating substantially all contamination by the elastomer.

BRIEF DESCRIPTION OF THE DRAWINGS

The objects of the present invention and the various features and details of the operation and construction thereof are hereinafter more fully set forth with reference to the accompanying drawings, where:

FIG. 1 is an enlarged sectional view of a conventional stopper fitted into a ring prior to undergoing a stopper surface coating process, all in accord with the invention;

FIG. 2 is a sectioned view taken on the line 2, 2 of FIG. 1 showing additional details of the assembly shown in FIG. 1;

FIG. 3 is an enlarged fragmentary sectional elevational view of the details contained within the dot and dash circle of FIG. 1 and designated FIG. 3;

FIG. 4 is a perspective view, of a ring;

FIG. 6a is an enlarge fragmentary sectional elevational view of the details contained within the dot and dash circle of FIG. 6 and designed FIG. 6a;

FIG. 7-12 illustrate additional rubber devices that are to be surface coated;

FIG. 13 is a partial plan view, illustrating a modification in the closure coating technique;

FIG. 14 is a side elevational view of FIG. 13; and

FIG. 15 is an enlarged fragmentary sectional elevational view taken on the line 15,15 of FIG. 13.

DETAILED DESCRIPTION OF THE PREFERRED EMBODIMENT

Figure 5:
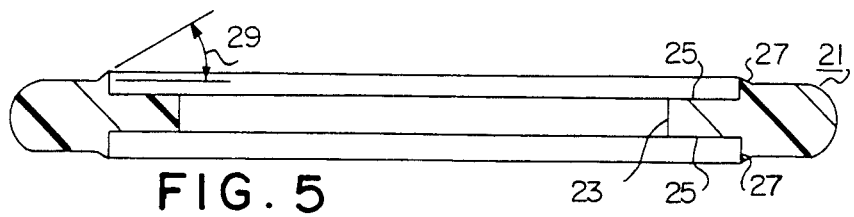
FIG. 5 is a sectional elevational view taken on the line 5,5 of FIG. 4 showing the geometry of the ring.

The devices of this invention may be manufactured from any conventional elastomeric base material, which has been used in pharmaceutical devices where an elastomeric component is required. Such materials are formed into rubber stoppers, plunger tips, prefilled syringes, sleeve stoppers, flashback bulbs, caps, liners, washers, and other elastomeric members which are in contact with the contents of a container in which there is a pharmaceutically pure material.

The elastomeric component of the pharmaceutical devices described herein may be manufactured from many of the elastomeric compounds which have conventionally been used in the pharmaceutical industry. Natural rubber, of course, was the original choice of materials for many elastomeric formulations and components in this as well as other industries. Butyl rubber and many of the synthetic elastomers have been successful used as stoppers, plunger tips, and the like, depending upon the requirements for stability during autoclaving or sterilization. A particular rubber which is admirably suited for the purposes of this invention is butyl rubber.

The present invention is intended to be used on all of the conventional preexisting stoppers and other elastomeric articles which are available in the pharmaceutical industry. Accordingly, any elastomeric base which has been used or which would be used if it possessed a barrier to extraction of undesirable components is therefore contemplated for use as the first component of the present invention. For the first time, elastomeric formulations which are otherwise unusable because of potential extraction problems may be now considered for use as pharmaceutical closures. Also for the first time, pharmaceuticals which could not be packaged in a vial with a rubber stopper are now able to be packages using the present invention.

Presently available rubber products are admirably suited for their purpose in the pharmaceutical industry, particularly in the ability to form an effective glass to rubber seal to preserve the integrity of the products. However, many of these same rubber products are unacceptable for contact with pharmaceutical solutions because metal ions and other contaminants may be extracted. Accordingly, the present invention seeks to improve the functionality of stoppers and the like in areas where it is lacking, while maintaining the functionality in all of the superior areas. Specifically, the invention contemplates improving the resistance to extraction of undesirable rubber product components while maintaining the highly desirable glass to rubber seal capabilities of the rubber products. The invention also contemplates the elimination of silicone, oil and other processing aids which have heretofore been used during the assembly of stoppers and containers.

The paraxylylenes which are intended for use in the present invention are described in the various patents discussed herein above. Specifically, as an example of various paraxylylene polymers and copolymers, the previous referenced Gorham U.S. Pat. Nos. 3,342,754 and 3,288,728 describe the chemistry of the polymers and copolymers which may be employed in the present invention. The Tittman et al U.S. Pat. Nos. 3,379,803 and 3,472,795 describe suitable methods for applying these particulars polymers and copolymers onto a wide variety of materials. It has been found that these processes generally are suitable for applying polymers and copolymers of paraxylylene to the elastomeric base materials contemplated in the present invention. The term polyparaxylylene is intended to include both polymers and copolymers of the various paraxylylenes which are described in the prior art.

The amount of polyparaxlylene will range from less than about 0.1 microns, to a preferred range of 0.5 to 1.0, to 5 or even 25 microns or more, depending on the particular needs and environment of the closure system.

Turning now to the drawings, a stopper 11 is shown in section in FIG. 1 with a region 13 where a syringe may be used for access to the contents of the container after the stopper has been inserted in a container. The stopper will be fitted into a vial or other container by inserting the annular inwardly extending protrusion 15 into the vial. The primary region where the stopper 11 seals against the glass container is the engagement region 17. An additional engagement region 19 provides additional sealing surface.

Figure 6:
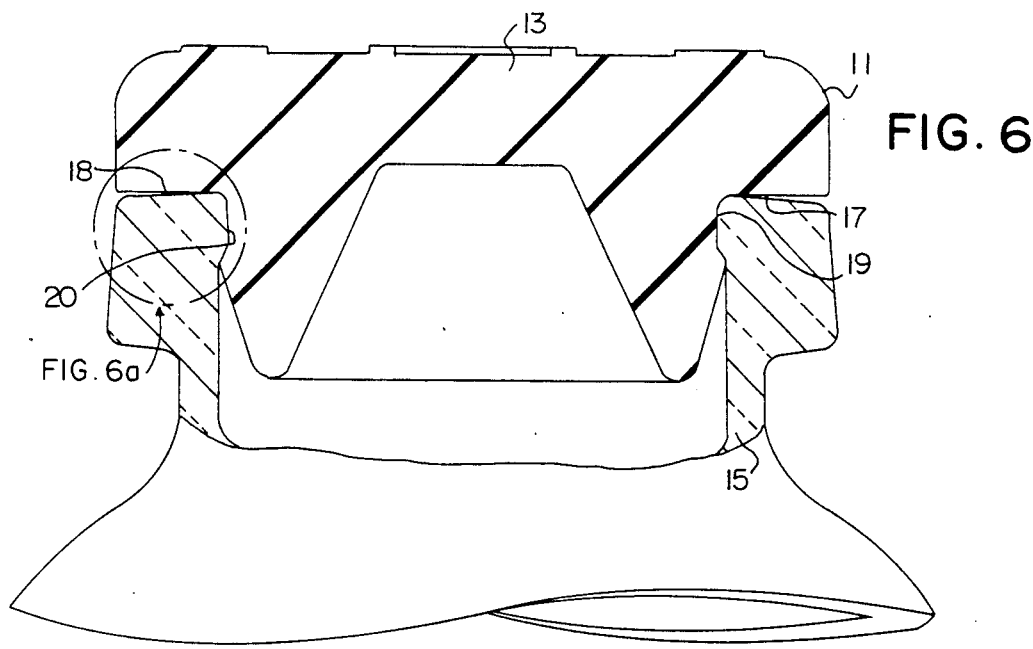
FIG. 6 is a fragmentary side elevational view of a vial whose opened terminal end is sealed by a stopper, the stopper having been surface coated, with the exception of a circumferentially extending band, created by the use of the ring.

As shown in FIG. 6, the stopper 11 has been inserted into a vial so that the annular face or terminal front of the container 18 contacts the container engaging region 17 and the annular inwardly extending portion 20 of the vial is sealed by contact with the additional container engaging region 19. The combination of stopper and container shown in FIG. 6 is the best arrangement yet discovered for use in pharmaceutical products. In accordance with the present invention, the admirable ability of the stopper 11 to seal to the container, particularly at areas 17-18 and 19-20 is maintained. In addition, the lower portion 15 is provided with a polyparaxlylene coating which prevents the extractions of unwanted contaminants from the elastomeric member 11.

In order to coat that portion of the stopper 11, which is exposed to the contents of the container, while not coating the container engaging regions 17 and 19, it has been discovered that an annular ring unit 21 may be fitted onto the stopper 11 prior to the time when the stopper is coated with the polyparaxylylene. Then the closure is coated, by tumbling the stoppers with a ring unit thereon, while polymerizing a paraxylylene polymer or copolymer as described above.

This process provides certain unique and important advantages. The ring unit 21 includes a radially extending face 23 which is in compressive contact with the elastomeric member 11 at the container engaging region 19. The ring unit 11 also includes an upward facing surface region 25 adjacent the container engaging region 17 so that an open spaced area exits between surface 25 and surface 17. During the polymerization process, no polyparaxylylene is formed in this region.

In a preferred embodiment, the ring unit 21 includes a rim 27 which radially inwardly increases the cross section of the ring 21 at the boundary between the coated and uncoated portions, as shown, for example, in FIG. 3. This rim 27 slightly deforms the elastomeric member 11 to ensure that the polymerization process does not deposit any polyparaxlylene on surface 17 of the elastomeric member 11. One particularly advantage which is achieved by this structure is that the difference between the elastomeric closure 11 and the ring 21 decreases as one moves radially inwardly to the rim 27. Thus, during a polymerization process, the thickness of the coating of polyparaxylylene decreases somewhat near the junction of the coated and uncoated surface to maximize the effectiveness of the glass to elastomer seal. As shown in FIG. 5, this angle, 29, is preferably less than 45°. As the rim 27 extends into or compresses the elastomer at its intersection with the elastomer, it can be seen that a very thin region is provided which will receive less of the paraxylylene coating than, for example, the lower portion 15 of the stopper 11. This is appropriate, of course, because only the interior coated portion 15 is in contact with the contents of the container.

The coating itself is far too thin to be visible. For illustration purposes, a coating C is shown in FIG. 6a which has been greatly enlarged to show a coating which has been formed on stopper 11 according to the invention. A boundary area exists on that part of the stopper 11 facing face 18 of the container extending up to uncoated region 17 on stopper 11. Here the coating C' has a decreasing cross section from the coated portion C to the uncoated portion 17. When, in one embodiment, the coating is applied with the ring unit 21, shown in FIG. 5 for example, rim 27 prevents any coating from being deposited radially inward from the point 27 a where rim 27 intersects stopper 11 along the engagement region 17 of stopper 11. The coating decreases in cross section from exposed coating C to point 27a in the boundary area facing end 18. Coating C' is illustrated in FIG. 6a, as one way for the cross section to decrease. Any decrease in cross section which is not a step function from a coated to an uncoated surface is within the scope of this invention. This is not true where there is no decrease in cross section from the coated to the uncoated portion other than a single step function.

Figure 7:
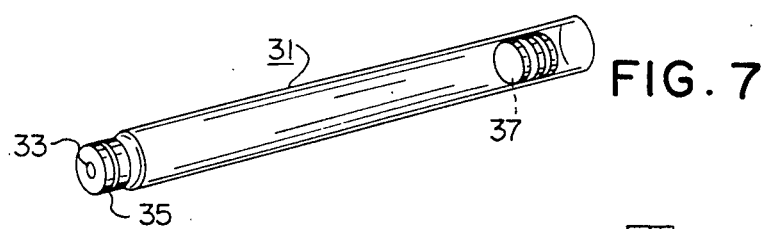
Figure 8:
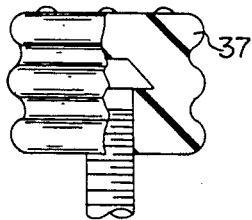

As was noted previously, various other elastomeric members which are used in the pharmaceutical industry can be provided with a polyparaxylylene coating over that portion which contacts pharmaceutical ingredients, while the portion of the elastomer in contact with the glass is uncoated. For example, in FIG. 7, a syringe 31 is shown having a rubber end 33, where the needle, not shown, will be inserted, and which is fastened to the syringe with a metal cap 35. Similarly, the plunger tip 37 can be coated on the portions in contact with the contents of the syringe 31 in accordance with the present invention. The plunger tip, shown partially in section in FIG. 8, contains portions which are in contact with the glass wall of the syringe 31 and which should be protected as is surface 19 of the stopper 11 as shown previously.

Figure 9:
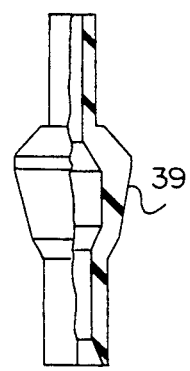
Figure 10:
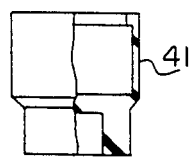
Figure 11:
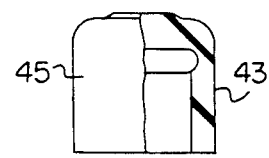

Similarly, flashback bulbs 39 as shown in FIG. 9, sleeve stoppers 41 as shown in FIG. 10 and elastomeric caps 43, which are covered by metallic tops 45, shown in FIG. 11 all can benefit from the concepts of the present invention. Shown in FIG. 12 is a double container arrangement in which the upper bottle and lower bottle include a dust cap 51, a rubber plunger 53, which is treated according to the principles of the present invention, an aluminum or other metal seal cap 55, and a center elastomeric seal 57.

FIGS. 13-15 show an alternative embodiment for applying the polyparaxylylene coating of the present invention to the regions of the elastomeric members which are to be in contact with the contents of the container while preventing polarization of the polyparaxylylene on the container engaging regions. Board 59 serves the same function as the ring unit 21. Stoppers 11a are inserted into holes in the board 59. The board 59 is shown in cross section in FIG. 15 and the rim 27a serves in the same manner as rim 27 does on the ring unit 21.

There are two directly competing objectives which are accomplished by the present invention. For the first time in the pharmaceutical industry, because of the present invention, it is possible to fully achieve both objectives. Specifically, it is possible to achieve an effective glass to elastomer seal which meets fully all of the requirement of the industry and at the same time substantially eliminate all concern for extractability.

As was noted above, Romberg et al U.S. Pat. No. 4,808,453 discloses a satisfactory method of coating elastomeric members, preferably at a range of about 0.5 to about 2.0 microns in thickness. This patent discloses an effective elastomeric closure which is successful in significantly decreasing the amount of extractable metals such as calcium, aluminum and zinc. See Tables 3 and 4 of the patent for example.

When compared to the prior art, the Romberg et al elastomeric closures are a significant advance in functionality. As noted above, stoppers prepared according to Gorham et al U.S. Pat. No. 3,300,332 are non functional as pharmaceutical closures. As mentioned above, four out of ten stoppers fail to seal at all. In contrast, the Romberg et al stoppers were able to achieve an effective seal in ten out of ten attempts. Nevertheless, even the Romberg et al U.S. Pat. No. 4,808,453 elastomeric closures do not completely replicate the effectiveness of the seals formed by uncoated elastomeric material.

Vacuum retention is a measurement of the quality of the seal. In this evaluation, stoppers are inserted into a vial while under vacuum. The vials are sealed and the vacuum in the vial is measured initially at 4 hours. The difference is calculated as a percentage of the vacuum remaining. This test is used to reproduce what is occurring in the lyophilization process, in which medicaments are freeze dried. Often times, vials which have been stoppered under vacuum may sit for as long as 4 hours until an aluminum cap seal is attached.

Nitrogen retention is another test which measures the quality of the seal. Vials are stoppered in a nitrogen atmosphere and allowed to sit for 4 hours without an aluminum cap seal being applied. The amount of oxygen in the vial, which enters through leakage from the atmosphere, is measured at both 0 hours time and at 4 hours lapsed time. The percentage gain has been the indication of the effectiveness of the seal.

A number of experiments were performed to evaluate the present invention and to demonstrate the surprising and unexpected results which are achieved in accordance with the invention. Both vacuum retention and nitrogen retention were measured to determine seal quality for six sets of elastomeric closure members. It is to be remembered that elastomers have demonstrated the ability to have a satisfactory seal because of the glass to rubber interface. The first set of closures were commercially available elastomers with no coating. The second, third and fourth set of closures were coated according to the Romberg et al U.S. Pat. No. 4,808,453, at 0.25 microns and 1.0 microns plus a coating of 25 microns. Finally, closures were prepared using the present invention. Specifically, elastomeric members were prepared having a first portion for contact with the container to form a seal and a second portion having a polyparaxylylene coating. One set of closures were made having a one micron thick coating and one set having a coating of 25 microns.

Presented below in Table I are the results of the seal quality tests. As is clear from an inspection of the data, the elastomer with no coating performed admirably and demonstrated expected outstanding seal quality. The prior art closures with extremely thin coatings showed some seal quality, while those in excess of the range described and claimed in the Romberg et al patent (those having 25 microns in thickness) failed the seal quality test completely. In fact, elastomeric closures having a polyparaxylylene coating of more than about 5 microns are unacceptable for use in the pharmaceutical industry since they are incapable of forming a seal. Finally, it is seen that the closures prepared in accordance with the present invention also had excellent seal quality. Of particular note is the elastomeric closure having a coating of 25 microns with essentially excellent seal quality. Thus, for the first time ever, an elastomeric closure having a coating thickness greater than 1 or 2 microns has an acceptable seal quality. This is truly unexpected and a significance advance in the art.

TABLE I

| | SEAL QUALITY | |
|---|---|---|
| Closure | Vacuum Retention | Nitrogen Retention |
| 1. Elastomer only | 100% | 0% |
| 2. Prior Art, 0.25 micron | 96% | 0.4% |
| 3. Prior Art, 1.0 micron | 50% | 6.0% |
| 4. Prior Art, 25 micron | Fail | Fail |
| 5. Invention, 1 micron | 98% | 0% |
| 6. Invention, 25 microns | 98% | 0% |

TABLE I-continued

Many elastomeric closures are completed by the addition of an aluminum cap seal to hold the elastomeric closure in place. These seals are more effective than simple elastomeric member and container evaluated above. In order to determine seal integrity, a method is used in which a solution is placed in a container, an elastomeric closure is inserted into the container and an aluminum seal cap is attached and crimped in place. The vial is then evaluated for leakage.

A test method was developed to evaluate seal integrity when a sealed container is subjected to vacuum while containing liquid solutions. Specifically, a solution of deionized water, sodium chloride and phenol is prepared and placed in ten glass vials of 10 cc capacity for each closure combination being evaluated. Six ml. of solution is added to the 10 cc. vial. The tops of each vial are wiped dry and stoppers are inserted into the vials. Aluminum seals are then crimped on the vials. Each vial is then weighed with a balance having four decimal place accuracy. The vials are inverted and placed in a vacuum chamber and maintained at a vacuum of 30 inches of mercury for 16 hours. The vials are then removed and weighed. The weight loss is then determined.

Presented below in Table II are the results of a series of tests evaluating elastomeric closures in the same way as was performed for Table I. Specifically, experiment no. 7 shows the weight loss for a closure in which the elastomeric member had no coating at all. Experiments 8, 9, and 10 show the results of using elastomeric closures according to the Romberg et al. U.S. Pat. No. 4,808,453 for coating the thickness of 0.25 microns and 1.0 microns, along with a stopper coated at 25 microns thickness, which is, of course, outside the scope of the Romberg et al patent. Finally, the two elastomeric closures coated according to the present invention at 1.0 microns and 25 microns were evaluated for seal integrity.

As can be seen from the data presented in Table II below, the excellent seal integrity of an elastomeric closure was duplicated using both of the elastomeric closures of the present invention. This is truly unexpected in view of the fact that the prior art closures were unacceptable except at the very smallest coating, and even that was four times less effective than the present invention.

TABLE II

| | SEAL INTEGRITY |
|---|---|
| Closure | Weight loss, m.g., 16 hrs. vacuum |
| 7. Elastomer only | 0.1 mg. |
| 8. Prior Art, 0.25 micron | 0.4 mg. |
| 9. Prior Art, 1.0 micron | 50 mg. |
| 10. Prior Art, 25 microns | fail |
| 11. Invention 1.0 micron | 0.1 mg. |
| 12. Invention | 0.1 mg. |

TABLE II-continued

| SEAL INTEGRITY | |
|---|---|
| Closure | Weight loss, m.g., 16 hrs. vacuum |
| 25 microns | |

While it is understood that most closures are not subjected to 16 hours of vacuum while inverted, so that the Romberg et al prior art stoppers of 0.25 microns and possibly 1.0 microns would be acceptable under ordinary storage conditions, it is a surprising and an unexpected result to see a significant improvement in seal integrity which is obtained using the present invention.

As has previously been noted herein, however, seal integrity is not the only criteria by which elastomeric closures are evaluated. Elastomeric closures made from synthetic and natural rubber, for example, have a potential for contaminating the contents of the pharmaceutical container. Catalysts, metals and organic components are extracted, resulting in two detrimental effects. If a sufficient amount of unwanted material is extracted, the contents are contaminated by a material which would be harmful. Therefore the stopper can not be used. Additionally, some of the materials which are extracted cause a reaction to take place, acting as a catalyst in some instances, which changes the nature of the medicine. Both concerns normally only occur to a minor and nominally insignificant amount. Nevertheless, it is desirable to eliminate contamination as much as possible. For example, in the prior art Romberg et al U.S. Pat. No. 4,808,453, remarkable improvement in metal extraction is shown using polyparaxylylene coatings.

In order to analyze the effects of coatings, particularly thick coatings on elastomeric closures, a series of tests were performed on a variety of elastomeric closures. Specifically, the stoppers were subjected to a soxhelet extraction in water for 16 hours. The amount of tributoxyethyl phosphate extracted in the water was then measured. That organic compound is present as an ingredient in the particular rubber formulation used. Present below in Table III are the results of these tests.

TABLE III

| WATER EXTRACTION OF ORGANICS | |
|---|---|
| Closure | Micrograms organic extracted |
| 13. Elastomer only | 96.8 |
| 14. Prior Art, 1.0 micron | 5.0 |
| 15. Prior Art,* 5.0 micron | 4.0 |
| 16. Prior Art* 25 microns | 0.9 |
| 17. Invention, 1 micron | 5.0 |
| 18. Invention, 5 microns | 4.0 |
| 19. Invention, 25 microns | 0.9 |

*Not able to function as stopper.

As can be seen, the experiment in which the elastomeric closure was uncoated produced a significant amount of organic extraction. When the method of the Romberg et al. prior art was employed, two of the tests were performed at significantly thicker coatings, namely 5.0 microns and 25 microns and both of these coatings were unable to function as a stopper. Not even a nominal seal was achieved.

In contrast, three sets of elastomeric closures were prepared according to the present invention. As can be seen, the effectiveness of a 25 micron coating on an elastomeric closure in accordance with the present invention produced a remarkable and surprising resistance to organic extraction. This same elastomeric closure, with 25 microns coating on that portion which may be in contact with the contents of a pharmaceutical component in a container, also demonstrated an ability to provide a seal of good quality and fine integrity.

In summary, the above experiments demonstrate that the present invention is capable of producing the ultimate elastomeric closure. For the first time, the previously opposite objectives of complete seal quality and integrity and complete prevention of extraction of the contents of the container have been achieved.

What is claimed is:

1. A device for use with containers, comprising an elastomeric member sized to engage the container, said member having a first portion for contact with said container to form a seal and a second portion having a polyparaxylylene coating of from 0.1 to 25.0 microns in thickness to form a barrier between said member and the contents of said container, said first and second portion having a boundary area wherein said coating has a decreasing cross section from said coated to said uncoated portion.

2. The device of claim 1, wherein said seal has a vacuum retention of at least above 96%.

3. The device of claim 1, wherein said seal has a seal integrity of about 0.1 mg.

4. The device of claim 1, wherein said coating is from 0.1 to 25.0 microns in thickness.

5. A closure device for containers, comprising an elastomeric closure member sized to engage the discharge bore of a container, said member having a first portion for contact with said bore to form a seal having a vacuum retention of at least 96%, and a second portion having a polyparaxylylene coating to form a barrier between said elastomeric member and the contents of the container, said coating being from about 0.1 to about 25 microns in thickness, said first and second portions having a boundary area wherein said coating has a decreasing cross section from said coated to said uncoated portion.

* * * * *